US009403916B2

(12) United States Patent
Lecommandoux et al.

(10) Patent No.: US 9,403,916 B2
(45) Date of Patent: Aug. 2, 2016

(54) POLYSACCHARIDE-AND POLYPEPTIDE-BASED BLOCK COPOLYMERS, VESICLES CONSTITUTED BY THESE COPOLYMERS AND USE THEREOF

(75) Inventors: Sébastien Lecommandoux, Canejan (FR); Jean-François Le Meins, Merignac (FR); Christophe Schatz, Ayguemorte les Graves (FR); Kamal Kumar Upadhyay, Mandideep (IN)

(73) Assignees: UNIVERSITE DE BORDEAUX, Bordeaux (FR); INSTITUT POLYTECHNIQUE DE BORDEAUX, Talence (FR)

( * ) Notice: Subject to any disclaimer, the term of this patent is extended or adjusted under 35 U.S.C. 154(b) by 0 days.

(21) Appl. No.: 13/126,589

(22) PCT Filed: Oct. 30, 2009

(86) PCT No.: PCT/FR2009/001263
§ 371 (c)(1),
(2), (4) Date: Apr. 28, 2011

(87) PCT Pub. No.: WO2010/049611
PCT Pub. Date: May 6, 2010

(65) Prior Publication Data
US 2011/0207686 A1 Aug. 25, 2011

(30) Foreign Application Priority Data
Oct. 30, 2008 (FR) ..................................... 08 06040

(51) Int. Cl.
*A61K 8/18* (2006.01)
*A61K 47/36* (2006.01)
*A61K 47/42* (2006.01)
*A61K 9/00* (2006.01)
*C08B 37/00* (2006.01)
*A61K 8/02* (2006.01)
*A61K 9/107* (2006.01)
*A61K 9/127* (2006.01)
*C08B 37/02* (2006.01)
*C08B 37/08* (2006.01)
*C08G 81/00* (2006.01)

(52) U.S. Cl.
CPC ............... *C08B 37/00* (2013.01); *A61K 8/0291* (2013.01); *A61K 9/0019* (2013.01); *A61K 9/1075* (2013.01); *A61K 9/1273* (2013.01); *C08B 37/0021* (2013.01); *C08B 37/0072* (2013.01); *C08G 81/00* (2013.01)

(58) Field of Classification Search
None
See application file for complete search history.

(56) References Cited

U.S. PATENT DOCUMENTS

| 2002/0131995 A1* | 9/2002 | Szoka, Jr. ...................... 424/450 |
| 2003/0054036 A1* | 3/2003 | Liggins et al. ................. 424/486 |
| 2007/0299227 A1* | 12/2007 | Gopferich et al. .......... 526/238.1 |
| 2008/0131510 A1* | 6/2008 | Gemeinhart et al. ......... 424/484 |
| 2010/0222407 A1* | 9/2010 | Segura et al. ................ 514/44 A |

FOREIGN PATENT DOCUMENTS

| WO | WO 2008001109 A2 | 1/2008 | |
| WO | WO2008/054081 | * 5/2008 | ............... A61K 9/22 |

OTHER PUBLICATIONS

Yang et al., Synthesis of Diblock Copolymers Consisting of Hyaluronan and Poly(2-ethyl-2-oxazoline), Macromolecules, 2005, 38, 2043-2046.*
Asayama et al., Synthesis of Novel Polyampholyte Comb-Type Copolymers Consisting of a Poly(L-lysine) Backbone and Hyaluronic Acid Side Chains for a DNA Carrier, Bioconjugate Chem. 1998, 9, 476-481.*
Liu and Zhang, Preparation of a polysaccharide-polyester diblock copolymer and its micellar characteristics, Carbohydrate Polymers, 69 (2007) 196-201.*
Sigma ProductInformation sheet for poly-γ-benzyl-L-glutamate, Sigma-Aldrich, Sep. 2003.*
Qiu & Bae, Polymer Architecture and Drug Delivery, Pharm. Res., vol. 23, No. 1, Jan. 2006.*
Zauner et al., Polylysine-based transfection systems utilizing receptor-mediated delivery, Adv. Drug Del. Rvws. 30 (1998) 97-113.*
Sigma Product Information for poly-γ-benzyl-L-glutamate (PBLG), Sigma-Aldrich, Sep. 2003.*
Albumin Release from Multiblock Copolymer Consisting of Poly(γ-benzyl L-glutamate) and Poly(ethylene oxide), Korea Polymer Jl., vol. 7, No. 3 pp. 203-207 (1999).*
A Review and Classification of Emerging Excipients in Parenteral Medications, Apte & Ugwu, Pharm. Tech., Mar. 2003, pp. 46-60.*
Auzenne et al. Hyaluronic acid-paclitaxel: antitumor efficacy against CD44(+) human ovarian carcinoma xenografts. Neoplasia. Jun. 2007; 9(6):479-86.*
Kwon & Kataoka, Block copolymer micelles as long-circulating drug vehicles, Adv. Drug Del. Rvws, 16 (1995) 295-309.*
Luo et al., A Hyaluronic Acid-Taxol Antitumor Bioconjugate Targeted to Cancer Cells, Biomacromolecules, 2000, 1, 208-218.*

(Continued)

*Primary Examiner* — Satyanarayana R Gudibande
*Assistant Examiner* — Joseph Fischer
(74) *Attorney, Agent, or Firm* — Browdy and Neimark, PLLC

(57) ABSTRACT

The invention relates to a new type of polysaccharide-block-polypeptide diblock copolymer which is bioresorbable or biodegradable and biocompatible, to a method for preparing same, to the micellar vesicles constituted of this copolymer, and to the use thereof for encapsulation, transport, vectorization, and targeting of molecules of interest.

14 Claims, 12 Drawing Sheets

(56) References Cited

OTHER PUBLICATIONS

Figure 1:
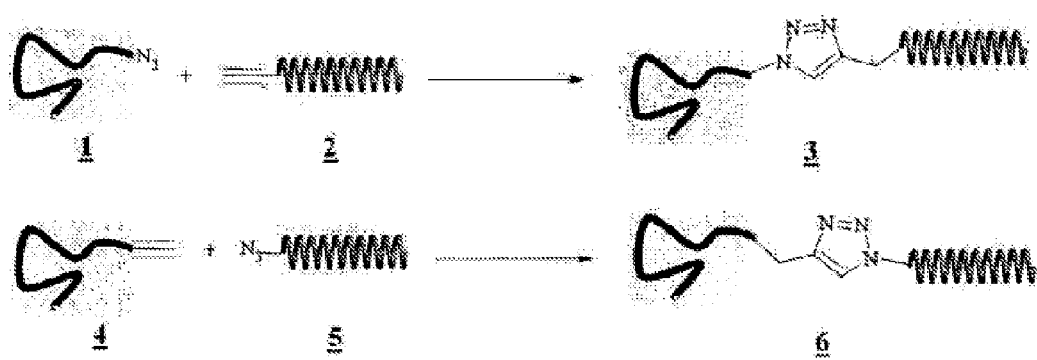

Crescenzi et al, Novel Hydrogels via Click Chemistry: Synthesis and Potential Biomedical Applications; Biomacromolecules 2007, 8, 1844-1850.*

Yang et al ., Synthesis of Diblock Copolymers Consisting of Hyaluranon and Poly(2-ethyl-2-oxazoline, Macromolecules 2005, 38, 2043-2046.*

Rodriguez-Hernandez, et al., "Reversible Inside-Out Micellization of pH-Responsive and Water-Soluble Vesicles Based on Polypeptide Diblock Copolymers", Journal of the American Chemical Society, Jan. 28, 2005, pp. 2026-2027, vol. 127.

Liu, et al., "Preparation of a polysaccharide-polyester diblock copolymer and its micellar characteristics", Carbohydrate Polymers, Mar. 30, 2007, pp. 196-201, vol. 69.

Agut, et al., "Synthesis of Block Copolypeptides by Click Chemistry", Macromolecular Rapid Communications, 2008, pp. 1147-1155, vol. 29.

Agut, et al., "A Versatile Synthetic Approach to Polypeptide Based Rod-Coil Block Copolymers by Click Chemistry", Macromolecules, 2007, pp. 5653-5661, vol. 40, No. 16.

Nakajima et al., Microheterophase Structure of the A-B-A Type Block Copolymer Consisting of α-Helical Poly(γ-benzyl L-glutamate) as the A Component and Polybutadiene as the B Component, American Chemical Society , 12 (5):844-848 (1979).

Hayashi, T. In: Developments in Block Copolymers-2, editor I. Goodman, Elsevier Applied Science Publishers, New York, Chapter 4, pp. 109-158 (1985).

Forster et al., Micellization of strongly segregated block copolymers, The Journal of Chemical Physics, 104 (24):9956-9970 (1996).

Kukula et al., The Formation of Polymer Vesicles or "Peptosomes" by Polybutadiene-block-poly(L-glutamate)s in Dilute Aqueous Solution, J. Am. Chem. Soc., 124(8):1658-1663 (2002).

Checot et al., Structure of Polypeptide-Based Diblock Copolymers in Solution: Stimuli-Responsive Vesicles and Micelles, Langmuir, 21:4308-4315 (2005).

Checot et al., Water-Soluble Stimuli-Responsive Vesicles from Peptide-Based Diblock Copolymers, Angew. Chem. Int. Ed., 41(8):1339-1343 (2002).

Checot et al., From supramolecular polymersomes to stimuli-responsive nano-capsules based on poly(diene-b-peptide) diblock copolymers, Eur. Phys. J. E, 10:25-35 (2003).

Babin et al., Self-assembled nanostructures from peptide—synthetic hybrid block copolymers: Complex, stimuli-responsive rod—coil architectures, The Royal Society of Chemistry, 128:179-192 (2005).

Rodriguez-Hernandez et al., Preparation of Shell Cross-Linked Nano-Objects from Hybrid-Peptide Block Copolymers, Biomacromolecules, 6:2213-2220 (2005).

Arimura et al., Formation of Core-Shell Type Biodegradable Polymeric Micelles from Amphiphilic Poly(aspartic acid)—block—Polylactide Diblock Copolymer, Biomacromolecules, 6:720-725 (2005).

Lubbert et al., Nonspherical Assemblies Generated from Polystyrene-b-poly(L-lysine) Polyelectrolyte Block Copolymers, Langmuir, 21(14):6582-6589 (2005).

Lazzari et al. editors, Block Copolymers in Nanoscience, WILEY-VCH Verlag GmbH & Co. KGaA, Chapter 6, pp. 117-150 (2006).

Douy et al., Synthesis and Ordered Structure of Amphipatic Block Copolymers with a Saccharide and a Peptide Block, Biopolymers, 19:493-507 (1980).

* cited by examiner

General synthesis diagram of the block copolymers. 1: polysaccharide nitride.
2: alkynated polypeptide. 4: alkynated polysaccharide. 5: polypeptide nitride. 3
and 6: polysaccharide-*block*-polypeptide block copolymers Size distribution of the vesicles of HYA-*b*-PBLG copolymer (hydrodynamic radius) obtained by dynamic light scattering.

Electron micrograph of vesicles of HYA-*b*-PBLG copolymer.

Scale bar = 200nm.

Size distribution of the vesicles of dextran-*b*-PBLG copolymer (hydrodynamic radius) obtained by dynamic light scattering Electron micrograph of vesicles of dextran-*b*-PBLG copolymer.

Kinetics of salting out of free doxorubicin (-o-) or encapsulated doxorubicin (-•-)

Kinetics of salting out of free docetaxel (-o-) or encapsulated docetaxel (-•-)

Observation of C6 cells after incubation for 24h in the presence of vesicles of hyaluronic acid-*block*-poly(γ-benzyl L-glutamate) filled with doxorubicin Capture of free doxorubicin and of encapsulated doxorubicin in the presence or in the absence of free hyaluronic acid in MCF-7 cells Tumour progression after single injection i.v. (5 mg/kg) of free or encapsulated doxorubicin Kaplan-Meier survival curve of animals with tumours after a single injection of free doxorubicin or of encapsulated doxorubicin

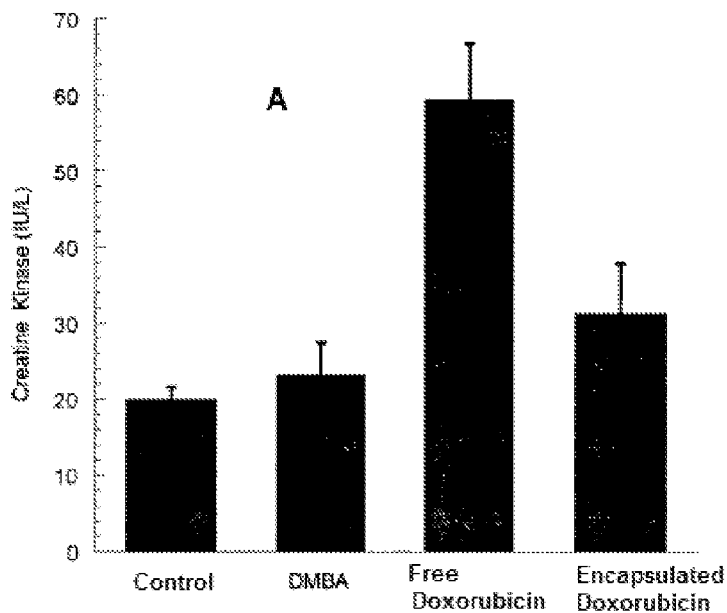
Figure 12 A
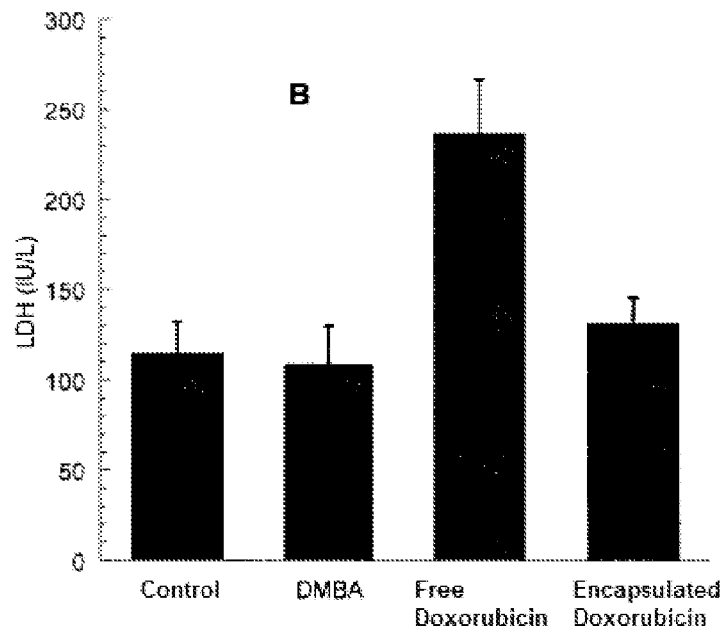
Figure 12 B
FIGURE 12
Serum levels of creatine kinase (A) and of lactate dehydrogenase (B) in healthy animals with tumours induced by DMBA, treated with free or encapsulated doxorubicin

POLYSACCHARIDE- AND POLYPEPTIDE-BASED BLOCK COPOLYMERS, VESICLES CONSTITUTED BY THESE COPOLYMERS AND USE THEREOF

The invention relates to a novel polysaccharide-block-polypeptide diblock copolymer, bioabsorbable or biodegradable and biocompatible, the preparation method thereof, micellar vesicles constituted by this copolymer, and use thereof for the encapsulation, transport, vectorization, and targeting of molecules of interest, natural or synthetic, with or without therapeutic activity.

Vesicular structures resulting from the assembly of amphiphilic biomolecules formed from lipids, proteins and carbohydrates exist naturally in living organisms. These natural vesicles are of variable size, with the largest performing the role of membranes that protect the intracellular contents from the extracellular environment, whereas small lipid vesicles perform the role of transporter of biomolecules within the cell.

It has been possible for stable vesicular structures to be prepared by synthesis, starting with liposomes in the 1960s, obtained by assembly of natural or synthetic phospholipids, up to the recent vesicles from polymers formed by assembly of synthetic block copolymers, called "polymersomes" (B. M. Discher et al., Science 1999, 284, 1143).

The "polymersomes" seem very promising for the development of biomedical applications, in particular for transporting therapeutic agents or as microreactors imitating the behaviour of living cells.

Moreover, "polymersomes" offer many advantages over liposomes, in particular a lower critical aggregation concentration, a unilamellar or multilamellar vesicular structure associated with a small size dispersion, and a higher membrane stability, reducing the passive release of the encapsulated molecules.

Moreover, the chemical diversity of the block copolymers means that infinite possibilities can be envisaged for modifying the properties of the vesicle to comply with the desired application.

Most of the "polymersomes" reported in the literature were formed by assembly of amphiphilic synthetic compounds, for example: polylactide-block-poly(ethylene oxide), poly(butadiene)-block-poly(ethylene oxide), polycaprolactone-block-poly(ethylene oxide) and poly(2-methyloxazoline)-block-poly(dimethylsiloxane)-block-poly(2-methyloxazoline), which have been investigated extensively in view of the biocompatibility or bioabsorbability of their respective blocks.

Scientific interest was then directed to assemblies comprising natural blocks, such as polypeptides or polysaccharides. In particular, the interest in polypeptide assemblies is based on the fact that they display unique physicochemical properties: they are naturally optically active, biocompatible and biodegradable in certain cases, they can be used for imitating natural polypeptide sequences, and are capable of undergoing reversible conformational transitions depending on the conditions of pH and/or temperature.

The block copolypeptides represent a particular subclass combining two synthetic polypeptide blocks that combine capacity for self-assembly and of highly ordered three-dimensional structures. They have been described in the literature as promising materials for applications such as biosensors, tissue engineering or selective release of active ingredients. The chemistry of polypeptide-based block copolymers has been investigated extensively in the literature, using ring-opening polymerization of N-carboxyanhydride (NCA) monomers of the corresponding amino acids, initiated by amino derivatives. By adapting Huisgen's technique of coupling by 1,3-dipolar cycloaddition, commonly called "click chemistry", the principle of which is based on formation of a disubstituted 1,2,3-triazole-1,4 bond, combining mild operating conditions, tolerance of the functional groups and a high yield, with copolymers of this type, polypeptide-based block copolymers were prepared, such as for example poly(γ-benzyl L-glutamate)-block-poly(ε-trifluoroacetyl-L-lysine) (D. Taton and S. Lecommandoux, Macromolecular Rapid Communications, 2008, 29, 1147).

Using more conventional chemical methods, other block copolypeptides have been synthesized, such as poly(L-glutamic acid)-block-poly(L-lysine) (J. Rodriguez-Hernandez and S. Lecommandoux, J.A.C.S, 2005, 127, 2026) or poly(L-lysine)-block-poly(L-leucine) (E. G. Bellomo et al., Nat. Mater., 2004, 3, 244) or poly(L-lysine)-block-poly(γ-benzyl-L-glutamate)-block-poly(L-lysine) (H. Iatrou et al., Biomacromolecules, 2007, 8, 2173).

With this chemistry it is possible to obtain very variable sizes of vesicles, in the range from 100 nm to several μm, by varying the operating conditions, as far as giant vesicles of up to 50 μm used as models of the membranes of living cells.

The chemistry of polysaccharide-based block copolymers has received far less study, owing to its complexity. A method of synthesis of dextran-block-polystyrene diblock copolymer by atom transfer radical polymerization (ATRP) was reported recently (C. Houga et al., Chem. Commun., 2007, 3063). Only a limited number of sugar-based block copolymer systems have been investigated, and there is little information available on their behaviour in solution and their properties.

For example, it has been described that dextran-block-poly (ε-caprolactone) self-assembles in water into polydisperse micellar structures having an average diameter of about 100 nm (J. Liu et al., Carbohydrate Polymers, 2007, 69, 196).

However, block copolymers combining a polypeptide segment and a polysaccharide block in a single linear chain have never been described or suggested in the literature.

It has now been found that it is possible, by synthesis of structures combining, in one copolymer, blocks of saccharide units and blocks of peptide units, to prepare compounds for imitating the natural glycoprotein structures that are involved in numerous biological mechanisms.

A glycoprotein is a protein bearing at least one polysaccharide group and a polypeptide chain. In unicellular or multicellular organisms, there are numerous glycoproteins on the external face of the plasma membrane, with the glycosylated moiety oriented towards the extracellular medium. Glycoproteins are present, in particular, in microorganisms such as viruses and bacteria. Thus, many pathogenic microorganisms have evolved to recognize the sugars present on the surface of cells and use them as points for anchorage and entry into the cells to be infected. For example, the HIV virus penetrates into the cells of the immune system by binding to membrane receptors such as the CXCR4 and CXCR5 receptors, which are glycoproteins.

Thus, it is particularly useful to have at our disposal synthetic biomimetic structures that can imitate the glycoproteins and are able to self-assemble in the form of vesicles. This makes it possible, for example, to form "synthetic viruses" imitating the structure of viruses and their functional role, and allowing efficient intracellular delivery of molecules of interest to be envisaged.

To achieve the synthesis of such complex structures, it was necessary to employ modern chemical reactions, which must be controlled particularly well, in particular reactions of "click chemistry" permitting effective and quantitative coupling of different chemical entities under mild conditions.

Therefore, according to a first aspect, the invention relates to a polysaccharide-block-polypeptide diblock copolymer constituted by a block of natural or synthetic saccharide units and a block of natural or synthetic peptide units.

By "block copolymer" is meant, like "diblock copolymer", a linear structure in which a polysaccharide block and a polypeptide block are joined by their ends.

Their linear structure is an advantageous characteristic of the copolymers according to the invention.

In fact, chemical modification of polymer chains (including peptide chains) on the side groups, which leads to grafted structures, can be carried out by simple chemical reactions. However, such modifications often result in poorly defined structures: variable number of grafts, homogeneous or heterogeneous distribution along the chain, lack of reproducibility, etc.

These major drawbacks are incompatible with industrial development, in particular in the pharmaceutical area. The linear structure of the copolymers according to the invention advantageously provides a high degree of control and reproducibility of the copolymer structure, thus ensuring regularity of properties.

This molecular control, together with prediction and control of the interfacial properties, makes it possible to form vesicles reproducibly and predictably.

Advantageously, the polysaccharide-block-polypeptide diblock copolymer according to the invention is bioabsorbable or biodegradable and biocompatible.

The expressions "block of saccharide units", "polysaccharide block" or "polysaccharide" can be used indiscriminately hereinafter to denote a chain of saccharide monomer units forming a polysaccharide or a polysaccharide derivative. Similarly, the expressions "block of peptide units", "polypeptide block" or "polypeptide" will be used indiscriminately to denote a chain of peptide monomer units forming a polypeptide or a polypeptide derivative.

The diblock copolymer according to the invention can comprise any type of natural or synthetic polysaccharide, or a derivative thereof, and any type of natural or synthetic polypeptide, or a derivative thereof.

By "polysaccharide derivatives" is meant the compounds resulting from a chemical modification of a polysaccharide, which can confer, for example, a hydrophobic character on a polysaccharide that is naturally hydrophilic, or, optionally, can add new functional groups onto the molecule.

Said derivatives can be, for example, ester or ether derivatives, in particular organic esters; inorganic esters such as phosphates or sulphates; non-ionic ether derivatives, such as, for example, alkyl, hydroxyalkyl or hydroxyalkaryl derivatives; ionic ether derivatives, such as, for example, sulphopropyl, carboxymethyl or (diethylamino)ethyl derivatives; or other derivatives such as conjugates of polysaccharides, para-toluenesulphonate, thiol or silylated derivatives.

Preferred polysaccharides can be selected, for example, from dextran, hyaluronic acid and derivatives thereof.

Polysaccharide derivatives and methods of modifying polysaccharides are described, for example, in the reference works "Polysaccharides I", Adv. Polym. Sci. (2005), 186, and "Polysaccharides II", Adv. Polym. Sci. (2006), 205.

By "polypeptide derivatives" is meant the compounds resulting from chemical modification of a polypeptide, which can confer, for example, a hydrophobic character on a polypeptide that is naturally hydrophilic, or, optionally, can add new functional groups onto the molecule.

Such derivatives can be, for example, ester or ether derivatives, in particular aliphatic or aromatic organic esters; inorganic esters; ether derivatives, such as, for example, alkyl or hydroxyalkyl derivatives, amide or imine derivatives, etc.

According to a preferred aspect, the polysaccharide-block-polypeptide diblock copolymer can comprise a polysaccharide block that has hydrophilic character and a polypeptide block that has hydrophobic character under physiological conditions, either naturally or by chemical modification endowing it with hydrophobicity.

According to another preferred aspect, the polysaccharide-block-polypeptide diblock copolymer can comprise a polysaccharide block that has hydrophobic character, in particular by chemical modification that can confer hydrophobicity on a naturally hydrophilic polysaccharide, and a polypeptide block that has hydrophilic character under physiological conditions.

For that reason, the polysaccharide-block-polypeptide diblock copolymers according to the invention are amphiphilic compounds capable of self-assembly to form a novel type of micellar vesicles assembled on the basis of natural or synthetic polymers. Relative to the existing vesicles, in particular liposomes, the applications of these vesicles based on polysaccharide-block-polypeptide diblock copolymers offer novel possibilities owing to the intrinsic properties of the polymers used.

In fact, the vesicles based on polysaccharide-block-polypeptide diblock copolymer in particular have the following advantages: biocompatible and bioabsorbable or biodegradable character, increased stability in aqueous solution, capacity for encapsulating hydrophilic and hydrophobic species, and a diversity of chemical functions that can easily be utilized to modify the surface of the vesicles and thus endow them with a particular property such as affinity for a biological receptor.

The use of particular polysaccharides or polypeptides having the property of being ligands of cellular receptors also makes it possible to prepare micellar vesicles permitting the targeted release of molecules of interest, where said polysaccharide can, by its nature, be involved in mechanisms of receptor-mediated endocytosis (RME).

The copolymers according to the invention can comprise, in particular, from 5 to 100 saccharide units and from 5 to 100 peptide units, in particular from 10 to 100 saccharide units and from 10 to 100 peptide units and, preferably, about 10 to about 50 saccharide units and about 10 to 50 peptide units. The weight ratio of hydrophilic polymer to hydrophobic polymer can be, for example, about 1/1.

Advantageous copolymers according to the invention have a molecular weight of 1000 to 50000 g/mol.

The polysaccharide can be selected, for example, from dextran, chitin, chitosan, hyaluronic acid, pullulan, fucan, sulphated fucan, succinoglycan, galactan, arabinogalactan, sulphated galactan, alginates, glucan, polysialic acid, heparin, heparan sulphate, chondroitin sulphate, acharan sulphate, keratan sulphate, dermatan sulphate, xanthan, pectin, xylan, amylose, amylopectin, cellulose, agarose, mannan, galactomannans, curdlan, arabinan, carrageenans, schizophyllan and derivatives thereof.

The polypeptide, in which the amino acid of which it is constituted can be in the optically active form L or D or in the racemic form DL, can be selected, for example, from poly(alanine), poly(arginine), poly(aspartic acid), poly(asparagine), poly(aspartate), poly(cysteine), poly(glutamic acid), poly(glutamate), poly(glutamine), poly(glycine), poly(histidine), poly(isoleucine), poly(leucine), poly(lysine), poly(methionine), poly(phenylalanine), poly(proline), poly(pyrrolysine), poly(selenocysteine), poly(serine), poly(threonine), poly(tryptophan), poly(tyrosine), poly(valine), poly(benzyl glutamate), poly(alkyl glutamate), poly(trifluoroacetyl-Lysine), poly(sarcosine), poly(hydroxyethyl-asparagine), poly(hydroxyalkyl-asparagine), poly(hydroxyalkyl-aspartamide), poly(benzyl aspartate) and derivatives thereof.

In a preferred aspect, said polypeptide is hydrophobic under physiological conditions.

Preferred hydrophobic polypeptides are, for example, poly(γ-benzyl-L-glutamate) and poly(ε-trifluoroacetyl-L-lysine).

According to another advantageous aspect, said polypeptide is hydrophilic under physiological conditions.

Preferred hydrophilic polypeptides are, for example, poly(L-glutamic acid), poly(L-glutamate) and poly(L-lysine).

For the purposes of the invention, the polypeptide can be obtained by a method of ring-opening polymerization of the N-carboxyanhydride (NCA) monomer of the corresponding amino acid, mentioned above.

According to a further aspect, the invention also relates to a preparation method of the bioabsorbable or biodegradable and biocompatible polysaccharide-block-polypeptide diblock copolymers described above.

As stated above, synthesis of the copolymers according to the invention employs well-controlled chemical reactions, in particular reactions from "click chemistry" permitting efficient and quantitative coupling under mild conditions.

Among the reactions from "click chemistry", there may be mentioned, for example, cycloadditions of unsaturated species (for example, 1,3-dipolar azide-alkyne cycloadditions, Diels-Alder reactions between a diene and a dienophile), reactions involving an electrophilic carbonyl group, of the non-aldol type (for example, formation of oxime ethers from an oxyamine, of hydrazones from a hydrazine, or of thiosemicarbazones from a thiosemicarbazine), reactions involving a thiol group (formation of thioethers from an alkene and mixed disulphides), reactions involving thiocarboxylic acid or thioester functions (formation of thioester and amide bonds) and Staudinger ligations involving phosphine and azide functions.

Each of the functional groups mentioned above can be introduced indiscriminately on the polypeptide group or on the polysaccharide group for coupling.

According to a preferred alternative, the method according to the invention for the preparation of polysaccharide-block-polypeptide diblock copolymers comprises the steps consisting of:
  subjecting said polysaccharide to a reductive amination so as to introduce an alkyne function at one end of the polysaccharide chain,
  introducing a nitride function at one end of the polypeptide chain, and
  coupling the polysaccharide chain and the polypeptide chain in a common solvent.

According to another alternative of the method according to the invention, said method comprises the steps consisting of:
  introducing an alkyne function at one end of the polypeptide chain,
  subjecting said polysaccharide to a reductive amination so as to introduce a nitride function at one end of the polysaccharide chain, and
  coupling the polypeptide chain and the polysaccharide chain in a common solvent.

The coupling of the polypeptide chain and of the polysaccharide chain, or vice versa, as well as the diblock copolymers with linear structure thus obtained, are shown diagrammatically in FIG. 1.

The preferred aspects of the invention relating to the polysaccharide-block-polypeptide diblock copolymers, as mentioned above, also apply to the preparation method thereof.

Reductive amination can be carried out, for example, by means of an amine such as propargylamine in the presence of a reducing agent such as sodium borocyanohydride.

The nitride function can be introduced at the end of the polypeptide chain by means of a bifunctional agent, such as 3-azidoaminopropane, the amine function serving to initiate ring-opening polymerization of the NCA monomer of the corresponding amino acid. The length of the polypeptide block can thus be controlled by the molar ratio of NCA monomer to bifunctional agent.

The solvent used for the step of coupling of the polysaccharide chain and polypeptide chain can be, for example, an organic solvent such as dimethylsulphoxide (DMSO). This reaction is preferably catalysed by copper derivatives, for instance CuBr, in the presence of a ligand, for example pentamethyldiethylenetriamine. The polypeptide or polysaccharide hydrophilic chain can be added in slight excess, of the order of 2 molar equivalents, then removed by dialysis, in order to ensure a quantitative coupling reaction and the formation of pure block copolymers.

According to a further aspect, the invention also relates to novel micellar vesicles formed from polysaccharide-block-polypeptide diblock copolymers constituted by a block of natural or synthetic saccharide units and a block of natural or synthetic peptide units, joined end-to-end in a linear chain structure, as described above.

Preferably, said copolymers comprise from 5 to 100 saccharide units and from 5 to 100 peptide units, in particular from 10 to 100 saccharide units and from 10 to 100 peptide units, and, preferably, about 10 to about 50 saccharide units and about 10 to about 50 peptide units.

Advantageously, said copolymers are bioabsorbable or biodegradable, and biocompatible.

As preferred polysaccharide and polypeptide, reference should be made to the preferred aspects of the invention relating to polysaccharide-block-polypeptide diblock copolymers, as mentioned above, which also apply to said micellar vesicles.

The micellar vesicles according to the invention can be prepared by various usual methods such as, for example, direct dissolution, film hydration, the emulsification/diffusion process or nanoprecipitation. Nanoprecipitation, which consists of mixing a solution of polymer in a water-miscible organic solvent, will preferably be used. Introduction of an organic solution of the diblock copolymer according to the invention in water with moderate stirring leads simultaneously to phase separation and a self-assembly process which progresses as the organic solvent diffuses in the aqueous phase, the latter being in excess relative to the organic phase. A suitable organic solvent is, for example, dimethylsulphoxide (DMSO) or formamide. After removing the organic solvent by evaporation and/or dialysis, the vesicles are recovered directly in aqueous solution. They can then be lyophilized in order to obtain them in the form of a redispersible dry extract. Their size can be modulated by adjusting the emulsification/diffusion or nanoprecipitation process (direction of addition, nature of the organic solvent, volume of the phases, concentration of copolymer, etc.).

Their size can also be easily controlled and adjusted depending on the desired application. It can in particular be reduced to about 100 nm after formation by the action of ultrasound or by extrusion on membranes of controlled porosity when a biomedical application is envisaged. In other applications, for example in the field of cosmetics, hygiene, cleaning or others, the vesicles according to the invention can have a size of the order of μm or of several tens of μm.

The micellar vesicles according to the invention can be characterized by dynamic and static light scattering, small-angle neutron scattering and transmission electron microscopy. These techniques for the characterization of micellar systems are described, for example, in G. Riess, *Progress in Polymer Science,* 2003, 28, 1107.

In an advantageous aspect, said micellar vesicle formed from polysaccharide-block-polypeptide diblock copolymers contains at least one molecule of interest, natural or synthetic, with or without therapeutic activity. This molecule can be introduced, depending on its polarity, in the aqueous phase or in the organic phase before the nanoprecipitation process. It is thus encapsulated during the manufacturing process of the vesicle. It can also be introduced after formation of the vesicles by pH gradient or emulsification/diffusion methods.

By "molecule having therapeutic activity" is meant, for example, a natural or synthetic molecule used for preventing or treating a pathology or for restoring a biological function, in vitro or in vivo, in particular in an animal, including a human being, or on isolated cells. Such molecules can be, for example, an active ingredient of a medicament, such as an antibiotic, an analgesic, an anti-inflammatory, an antitumour agent, etc., or a peptide, a protein, a hormone, an enzyme, a nucleic acid, an oligonucleotide, an antigen, an antibody, an interferon, a growth factor, a modulator of enzyme activity, a cell receptor activator or inhibitor, a vitamin etc.

Such molecules having therapeutic activity can be used, for example, in the pharmaceutical or medical field.

If appropriate, encapsulation of said molecule having therapeutic activity in a micellar vesicle according to the invention makes it possible to decrease significantly the toxicity of said molecule. In particular, the well-documented toxicity of the antitumour agents, such as, in particular, their cardiotoxicity, for example when using doxorubicin or mitoxantrone or their neurotoxicity, for example when using vincristine, can be reduced significantly.

By "molecule of interest not having therapeutic activity" is meant, for example, a natural or synthetic molecule which is not used for preventing or treating a pathology or restoring a biological function, in vitro or in vivo, in particular in an animal, including a human being, or on isolated cells. If appropriate, such a molecule can nevertheless have a biological activity, in particular with respect to plants or microorganisms. There may be mentioned, by way of non-limitative examples, the following fields of application:
    medical imaging: diagnostic agents, for example, contrast media, isotopes, fluorescent probes
    cosmetics and hygiene: olfactory molecules, pigments, colorants, antioxidants, antibacterials, antiseptics, emollients, exfoliating agents, hydrating agents, etc;
    cleaning and detergency: surfactants, colorants, antioxidants, antibacterials, antiseptics, bleaching agents, etc;
    plant protection chemicals: pesticides, fungicides, herbicides, insecticides, growth accelerators, etc.,
    food industry: colouring matter, flavour enhancers etc.,
    organic chemistry: organic, metallic or inorganic catalytic derivatives, etc.,
or in any other field of activity in which it is desired to encapsulate a molecule in a micellar vesicle, the latter offering the advantage of being bioabsorbable or biodegradable and biocompatible.

The use of the micellar vesicles formed from polysaccharide-block-polypeptide diblock copolymers constituted by a block of natural or synthetic saccharide units and a block of natural or synthetic polypeptide units, as described above, as vehicles for encapsulation, transport, vectorization and/or targeting of at least one molecule of interest, natural or synthetic, with or without therapeutic activity, represents another aspect of the invention.

The invention also relates to pharmaceutical compositions comprising micellar vesicles formed from polysaccharide-block-polypeptide diblock copolymers constituted by a block of natural or synthetic saccharide units and a block of natural or synthetic polypeptide units, and containing at least one molecule of interest, natural or synthetic, with or without therapeutic activity, as described above, and a pharmaceutically acceptable excipient.

The pharmaceutically acceptable excipients can be selected, depending on the method of administration envisaged, from the usual excipients in the pharmaceutical field.

For example, for oral administration in the form of tablets, the excipients can be selected from binders, fillers, disintegrants, adjuvants or retardants, and for administration by the oral route in the form of aqueous or oily suspensions, solutions or emulsions, the compositions can also contain suspending agents; emulsifiers, non-aqueous vehicles or preservatives.

For parenteral administration, the pharmaceutical compositions can be in the form of sterile aqueous and non-aqueous injectable solutions that can contain antioxidants, buffers, bacteriostatic agents and solutes which make the formulation isotonic with the blood of the chosen recipient; or in the form of sterile aqueous or non-aqueous suspensions that can comprise suspending agents and thickeners.

The pharmaceutical compositions according to the invention can also be administered by other routes, such as the buccal or sublingual route by means of a suitable excipient, the topical route on the epidermis, in the form of cream, gel, ointment, lotion or transdermal patch, the intranasal route, in the form of a spraying liquid, powder or drops or by inhalation, by means of a suitable propellant.

Advantageously, the micellar vesicles according to the invention can also be used for encapsulation both of hydrophobic molecules and hydrophilic molecules, as they possess two compartments of different polarity, namely the membrane, which is hydrophobic, and the internal cavity, which is hydrophilic. Moreover, as the self-assembly of the copolymers into vesicles takes place by weak interactions, the dissociation of the vesicles and the concomitant release of the encapsulated molecule of interest can be obtained under defined conditions (salinity, temperature, pH, hydrolysis, etc.)

According to a preferred aspect of the invention, said micellar vesicle is formed from a polysaccharide-block-polypeptide diblock copolymer in which the polysaccharide displays affinity for at least one cellular receptor.

According to another preferred aspect of the invention, said micellar vesicle is formed from a polysaccharide-block-polypeptide diblock copolymer in which the polypeptide displays affinity for at least one cellular receptor.

In such cases, the micellar vesicles can advantageously be used for targeting a molecule of interest.

Among the polysaccharides of this type, there may be mentioned, for example, hyaluronic acid, which displays affinity for the CD44 receptors. The CD44 receptors are present at elevated levels in tumour cells of various carcinomas, melanomas, lymphomas etc. ("Chemistry and Biology of Hyaluronan", H. G. Garg and C. A. Hales Ed. (2004), Chapter 5, Elsevier Ltd.).

Polypeptides of interest in this respect are, for example, poly(glutamic acid) or poly(glutamate). In fact, poly (glutamic acid) or poly(glutamate) are, for example, ligands of glutamate receptors (Mornet C, Briley M, Trends Pharmacol Sci. 1988; 9:278-279) or of TLR4 receptors (Poo et al. 22 (2) 517—The FASEB Journal).

In another preferred aspect, said micellar vesicle is formed from a polysaccharide-block-polypeptide diblock copolymer in which said polysaccharide may be involved in a mechanism of receptor-mediated endocytosis (RME).

Alternatively, said micellar vesicle is formed from a polysaccharide-block-polypeptide diblock copolymer in which said polypeptide may be involved in a mechanism of receptor-mediated endocytosis.

Receptor-mediated endocytosis is a biological mechanism by which molecules present in the extracellular space bind to cellular receptors and are internalized, also permitting targeting of a molecule of interest.

A polysaccharide of interest for the purposes of the invention is arabinogalactan, which interacts with hepatocyte receptors involved in mechanisms of mediated endocytosis.

Polysaccharides that may be involved in mechanisms of receptor-mediated endocytosis are mentioned, for example, in U.S. Pat. Nos. 5,336,506 and 5,554,386.

The invention is illustrated but is not limited by the examples given below.

EXAMPLE 1

Preparation of a Hyaluronic Acid-Block-Poly(γ-Benzyl L-Glutamate) Diblock Copolymer

Preparation of Poly(γ-Benzyl L-Glutamate) Having a Nitride Function (PBLG-Nitride)

6 g (22.81 mmol) of γ-benzyl L-glutamate N-carboxyanhydride is introduced under an argon atmosphere into a flask of the Schlenk type previously flamed under vacuum, and dissolved in 60 ml of anhydrous DMF. The solution is stirred for 10 min and 57 µL of 1-azido-3-aminopropane (570 µmol) is added by means of a syringe purged with nitrogen. The solution is stirred for 40 h under vacuum at ambient temperature. The polymer is recovered by precipitation from diethyl ether and then dried under vacuum. The mass of product recovered is 4.2 g (yield: 70%). Analysis by proton NMR spectroscopy shows a number-average degree of polymerization of 23. $^1$H NMR analysis (CDCl$_3$: deuterated trifluoroacetic acid, 85:15): 1.8 ppm (N$_3$—CH$_2$—CH$_2$—CH$_2$—, 2H); 1.9 and 2.1 ppm (—CH$_2$—CH$_2$—CH—, 2H); 2.5 ppm (—CH$_2$—CO, 2H); 2.6 ppm (N$_3$—CH$_2$—CH$_2$—CH$_2$—, 2H); 3.4 ppm (N$_3$—CH$_2$—CH$_2$—CH$_2$—, 2H); 4.6 ppm (—NH—CH—CO—, 1H); 5.1 ppm (—CH$_2$—C$_6$H$_5$, 2H); 7.3 ppm (—C$_6$H$_5$, 5H); 7.9 ppm (NH, 1H).

Preparation of Hyaluronic Acid Having an Alkyne Function (Alkynated Hyaluronic Acid)

Hyaluronic acid (2.2 g; 6×10$^{-4}$ mol) having a number-average degree of polymerization equal to 10 is dissolved in an acetate buffer (pH=5.6) to a concentration by weight of 2%. 2.82 mL (4.4×10$^{-2}$ mol) of propargylamine and 2.77 g (4.4×10$^{-2}$ mol) of sodium borocyanohydride are added to the mixture with stirring. After reaction for 5 days at 50° C. and with stirring, the reaction mixture is concentrated in a rotary evaporator and precipitated from 400 mL of cold methanol. The solid is recovered by centrifugation and washed with cooled methanol to remove the excess propargylamine and sodium borocyanohydride. The precipitate is then dried under vacuum for 2 days. The mass of product recovered is 2.2 g (yield: 100%). $^1$H NMR analysis (D$_2$O): 3.35 ppm (C(2)H, GlcA); 3.59 ppm (C(3)H, GlcA); 3.72 ppm (C(5)H, GlcA); 3.73 ppm (C(4)H, GlcA); 4.48 ppm (C(1)H, GlcA); 2.03 ppm (CH$_3$, 3H, GlcNAc); 3.50 ppm (C(5)H, GlcNAc); 3.55 ppm (C(4)H, GlcNAc); 3.72 ppm (C(3)H, GlcNAc); 3.86 ppm (C(2)H, GlcNAc); 3.90 ppm (C(6)H, GlcNAc); 4.54 ppm (C(1)H, GlcNAc); 8.22 ppm (NH, GlcNAc); 3.72 ppm (C(3)H, β, GlcNAc); 3.83 ppm (C(2)H, β, GlcNAc); 3.91 ppm (C(3)H, α, GlcNAc); 4.05 ppm (C(2)H, α, GlcNAc); 4.73 ppm (C(1)H, β, GlcNAc); 5.16 ppm (C(1)H, α, GlcNAc); 8.41 ppm (NH, α, GlcNAc); 8.47 ppm (NH, β, GlcNAc).

Preparation of Hyaluronic Acid-Block-Poly(γ-Benzyl L-Glutamate) Copolymer

Two equivalents of alkynated hyaluronic acid (2.1 g; 4.2×10$^{-4}$ mol) and one equivalent of PBLG nitride (1.05 g; 2.1×10$^{-4}$ mol) are solubilized in 70 mL of anhydrous DMSO. The mixture is stirred for 20 min and then 87.04 µL of pentamethyldiethylenetriamine (4.1×10$^{-4}$ mol) is added under a nitrogen atmosphere. The mixture is then degassed 3 times by cycles of freezing/thawing and transferred under nitrogen to a flask of the Schlenk type containing CuBr (60 mg; 4.18×10$^{-4}$ mol). The reaction mixture is stirred at 60° C. for 3 days and then dialysed against milliQ water at pH 3.5 using a 6 Spectra/Por® dialysis membrane characterized by a cut-off threshold of 50 kDa. The copolymer is then recovered by centrifugation and dried under vacuum for two days. The mass of product recovered is 1.5 g (yield: 70%). $^1$H NMR analysis (DMSO d$_6$—60° C.): 1.8 ppm (CH$_3$, GlcNAc); 1.9 ppm (—N$_3$—CH$_2$—CH$_2$—CH$_2$—, 2H); 2.05 and 2.25 ppm (—CH$_2$—CH$_2$—CH—, 2H); 2.5 ppm (CH$_2$—CO—, 2H); 2.65 ppm (—N$_3$—CH$_2$—CH$_2$—CH$_2$—, 2H); 3.1 ppm (C(2)H, GlcA); 3.2 ppm (C(3)H, GlcA); 3.1-3.7 ppm (C(3)H, C(4)H, C(5)H, 3H, GlcNAc); 3.5 and 3.7 ppm (C(6)H, GlcNAc); 3.1-3.7 ppm (C(4)H, C(5)H, 2H, GlcA); 3.5 and 3.7 ppm (C(2)H, α and β, GlcNAc); 4.2 and 4.35 ppm (C(1)H, α and β, GlcA); 4.58 ppm (C(1)H, GlcNAc); 4.6 ppm (—NH—CH—CO, 1H); 5 ppm (—CH$_2$—C$_6$H$_6$, 2H); 7.25 ppm (—C$_6$H$_5$, 5H); 7.6 ppm (—N$_3$—C(CH$_2$)=CH—, 1H); 8.2 ppm (—NH—CH—CO—, 1H).

EXAMPLE 2

Preparation of a Dextran-Block-Poly(γ-Benzyl L-Glutamate) Diblock Copolymer

Preparation of Dextran Having an Alkyne Function (Alkynated Dextran)

3 g of dextran (4.54×10$^{-4}$ mol) having a number-average degree of polymerization equal to 40 is introduced into a flask equipped with a condenser and dissolved by magnetic stirring in an acetate buffer adjusted to pH=5 to a final concentration of polymer of 2 wt. %. Propargylamine is added in large excess (2.5 g; 4.54×10$^{-4}$ mol) with stirring. Once the medium is homogeneous, the reducing agent (NaBH$_3$CN) is added to the reaction mixture in large excess (2.85 g; 4.54×10$^{-4}$ mol). The solution is stirred vigorously in a bath at 50° C. for 5 days with the daily addition of a defined amount of reducing agent (25 molar equivalents relative to dextran). The reaction mixture is then concentrated in a rotary evaporator and then dialysed against water using a 6 Spectra/Por® dialysis membrane characterized by a cut-off threshold of 2 kDa. The polymer is finally recovered by lyophilization. The mass of polymer obtained is 2.24 g, i.e. a yield by weight of 74%. $^1$H NMR analysis (DMSO $d_6$): 3.17 ppm (C(4)H); 3.2 ppm (C(2)H); 3.42 ppm (C(3)H); 3.5 and 3.75 ppm (C(6)H, 2H); 3.62 ppm (C(5)H); 4.5 ppm (C(2)OH); 4.65 ppm (C(1)H); 4.85 ppm (C(3)OH); 4.95 ppm (C(4)OH).

Preparation of Dextran-Block-Poly(γ-Benzyl L-Glutamate) Copolymer

Two equivalents of alkynated dextran (0.4 g; $6.06 \times 10^{-5}$ mol) and one equivalent of PBLG-nitride (0.147 g; $3.03 \times 10^{-5}$ mol) are solubilized in 25 mL of anhydrous DMSO. The mixture is stirred for 20 min and then 12.6 µL of pentamethyldiethylenetriamine ($6.06 \times 10^{-5}$ mol) is added under a nitrogen atmosphere. The mixture is then degassed 3 times by cycles of freezing/thawing and transferred under nitrogen to a flask of the Schlenk type containing CuBr (9 mg; $6.06 \times 10^{-5}$ mol). The reaction mixture is stirred at ambient temperature for 3 days and then dialysed against milliQ water using a 6 Spectra/Por® dialysis membrane characterized by a cut-off threshold of 50 kDa. The copolymer is then recovered by lyophilization. The mass of product recovered is 0.302 g (yield: 87%). $^1$H NMR analysis (DMSO $d_6$): 1.9 ppm (—N$_3$—CH$_2$—CH$_2$—CH$_2$—, 2H); 2 and 2.15 ppm (—CH$_2$—CH$_2$—CH—, 2H); 2.45 ppm (CH$_2$—CO—, 2H); 2.65 ppm (—N$_3$—CH$_2$—CH$_2$—CH$_2$—, 2H); 3.1 ppm (N$_3$—CH$_2$—CH$_2$—CH$_2$, 2H); 3.15 ppm (C(4)H); 3.17 ppm (C(2)H); 3.42 (C(3)H); 3.5 and 3.75 ppm (C(6)H, 2H); 3.62 ppm (C(5)H); 4.5 ppm (C(2)OH); 4.65 ppm (C(1)H); 4.88 ppm (C(3)OH)); 4.9-5 ppm (C(4)OH); 7.2 ppm (C$_6$H$_5$, 5H); 8.25 ppm (—NH—CH—CO—, 1H).

EXAMPLE 3

Preparation of a Dextran-Block-Poly(ε-Trifluoroacetyl-L-Lysine) Diblock Copolymer Preparation of Poly(ε-Trifluoroacetyl-L-Lysine) Having a Nitride Function (Poly(ε-Trifluoroacetyl-L-Lysine)-Nitride)

2 g ($7.46 \times 10^{-3}$ mol) of ε-trifluoroacetyl-L-lysine N-carboxyanhydride is introduced under an argon atmosphere into a flask of the Schlenk type previously flamed under vacuum, and dissolved in 21 mL of anhydrous DMF. The solution is stirred for 10 min and 9 µL of 1-azido-3-aminopropane (94 µmol) is added by means of a syringe purged with nitrogen. The solution is stirred for 40 h under vacuum at ambient temperature. The polymer is recovered by precipitation from diethyl ether and then dried under vacuum. The mass of product recovered is 1.5 g (yield: 75%). Analysis by proton NMR spectroscopy shows a number-average degree of polymerization of 64.

$^1$H NMR analysis (DMSO $d_6$): 1.1-2 ppm (—CH—CH$_2$—CH$_2$—CH$_2$—CH$_2$—NH—, 6H); 3.12 ppm (CO—NH—CH$_2$—, 2H); 3.8 ppm (CO—CH—NH, 1H); 8.2 ppm (—NH—CH—CO—, 1H); 9.3 (CF$_3$—CO—NH—, 1H).

Preparation of Dextran-Block-Poly(ε-Trifluoroacetyl-L-Lysine) Copolymer

Two equivalents of alkynated dextran (0.4 g; $6.06 \times 10^{-5}$ mol) and one equivalent of poly(ε-trifluoroacetyl-L-lysine)-nitride (0.271 g; 3.03 $10^{-5}$ mol) are dissolved in 30 mL of anhydrous DMSO. The mixture is stirred for 20 min and then 12.6 µL of pentamethyldiethylenetriamine ($6.06 \times 10^{-5}$ mol) is added under a nitrogen atmosphere. The mixture is then degassed 3 times by cycles of freezing/thawing and transferred under nitrogen to a flask of the Schlenk type containing CuBr (9 mg; $6.06 \times 10^{-5}$ mol). The reaction mixture is stirred at ambient temperature for 3 days and then dialysed against milliQ water using a 6 Spectra/Por® dialysis membrane characterized by a cut-off threshold of 50 kDa. The mass of product recovered after lyophilization is 0.320 g (yield: 67%). $^1$H NMR analysis (DMSO $d_6$): 1.1-2 ppm (—CH—CH$_2$—CH$_2$—CH$_2$—CH$_2$—NH—, 6H); 3.12 ppm (CO—NH—CH$_2$—, 2H); 3.15 ppm (C(4)H); 3.17 ppm (C(2)H); 3.42 (C(3)H); 3.5 and 3.72 ppm (C(6)H, 2H); 3.62 ppm (C(5)H); 3.8 ppm (CO—CH—NH, 1H); 4.5 ppm (C(2) OH); 4.65 ppm (C(1)H); 4.88 ppm (C(3) OH)); 4.9-5 ppm (C(4) OH); 8.2 ppm (—NH—CH—CO—, 1H); 9.3 (CF$_3$—CO—NH—, 1H).

EXAMPLE 4

Preparation of Micellar Vesicles Based on Hyaluronic Acid-Block-Poly(γ-Benzyl L-Glutamate) Copolymer The hyaluronic acid-block-poly(γ-benzyl L-glutamate) copolymer from Example 1 is dissolved in DMSO at 55° C. at a concentration of 5 mg/mL and injected by means of a syringe pump at 18 mL/h in one volume of Tris buffer (10 mM, pH=7.4; [NaCl]=145 mM) up to a final concentration of copolymer of 1 mg/mL. The organic solvent is removed by dialysis against a tris buffer (10 mM, pH=7.4; [NaCl]=145 mM) using a dialysis membrane (6 Spectra/Por®) having a molecular weight cut-off threshold of 2 kDa. A solution of vesicles is thus obtained and is characterized by dynamic and static light scattering, small-angle neutron scattering and transmission electron microscopy.

Polymer vesicles are thus obtained with a radius of 200 nm and with a narrow size distribution, and having a membrane thickness of about 9 nm.

Figure 2:
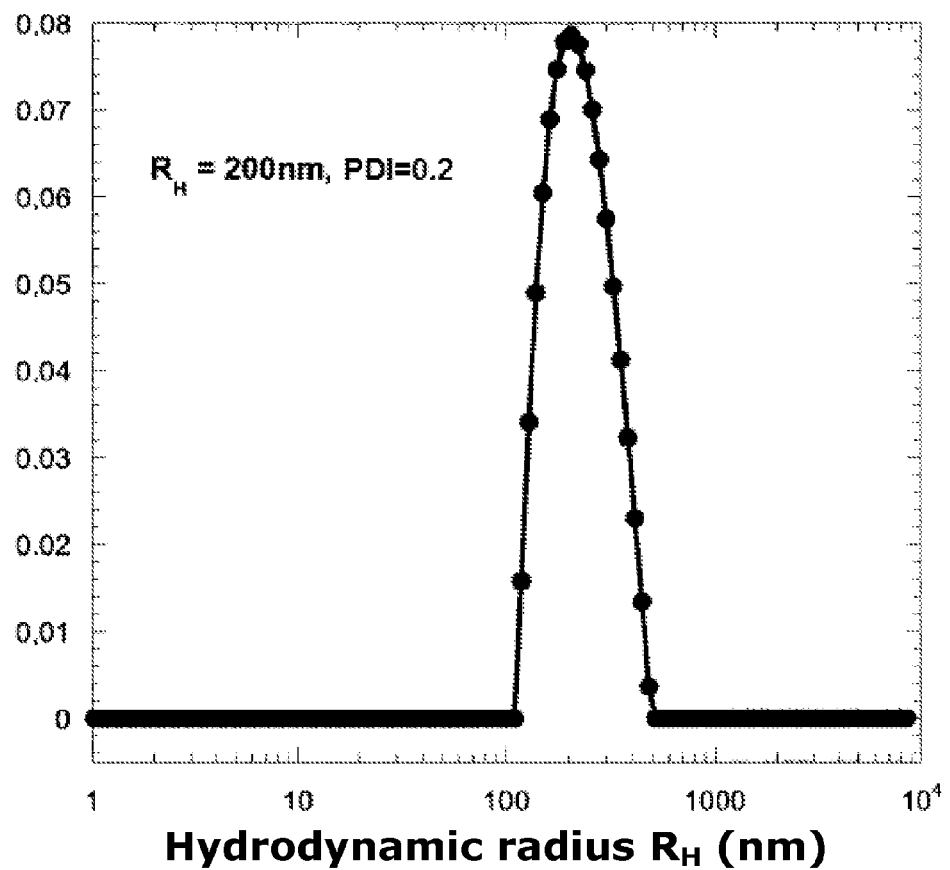
Figure 3:
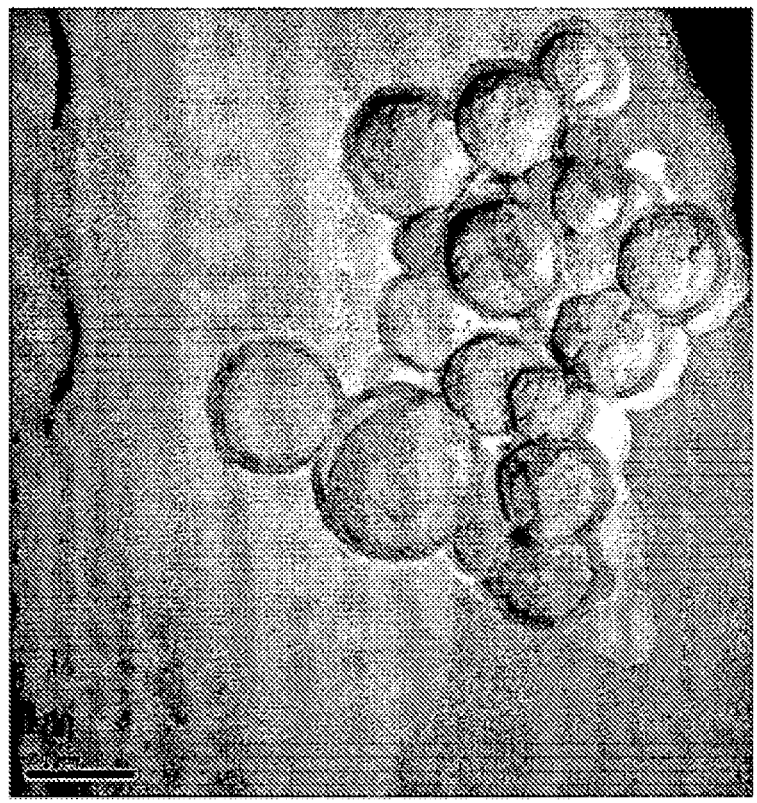

FIG. 2 shows the size distribution of the vesicles (hydrodynamic radius) obtained by light scattering. FIG. 3 shows an image from transmission electron microscopy obtained for these same vesicles.

EXAMPLE 5

Preparation of Micellar Vesicles Based on Dextran-Block-Poly(γ-Benzyl L-Glutamate) Diblock Copolymer The dextran-block-poly(γ-benzyl L-glutamate) copolymer from Example 2 is dissolved in 1 mL of DMSO at a concentration of 0.5 mg/mL, then 9 mL of water milliQ is added gradually by means of a syringe pump at 18 mL/h with stirring. The DMSO is then removed by dialysis against milliQ water using a 6 Spectra/Por® dialysis membrane characterized by a cut-off threshold of 2 kDa. The vesicles that formed are analysed by dynamic light scattering and transmission electron microscopy.

Polymer vesicles are thus obtained with a radius of 40 nm and with a narrow size distribution.

Figure 4:
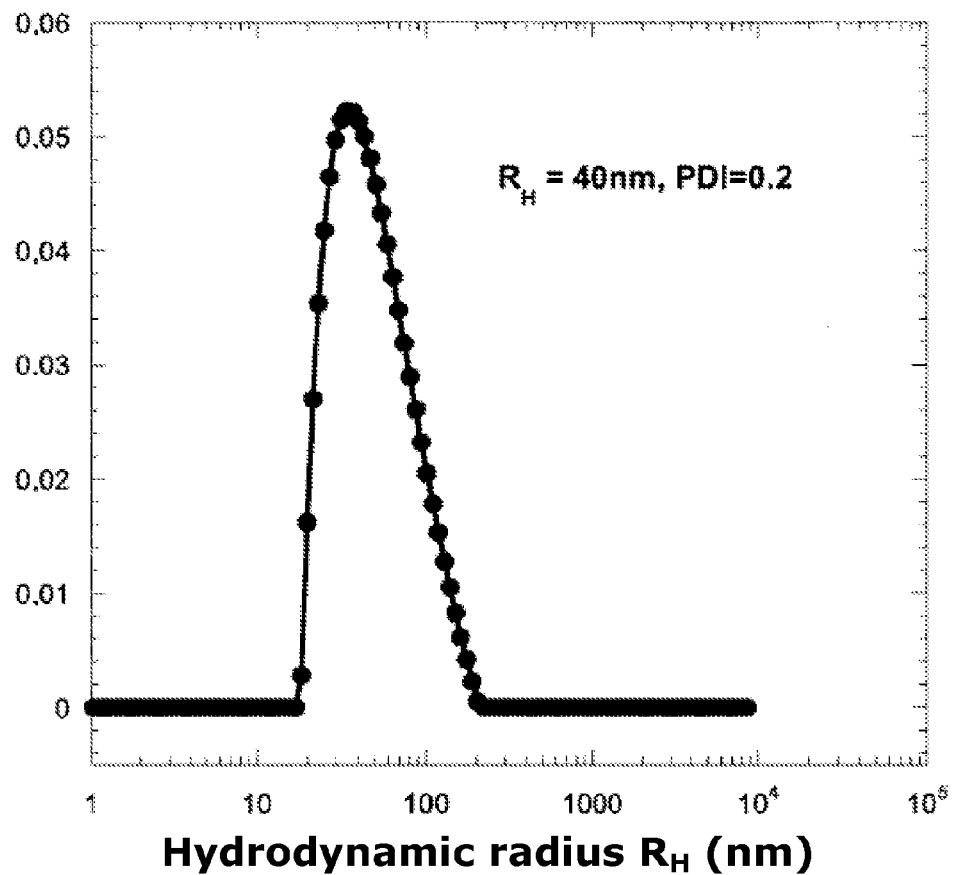
Figure 5:
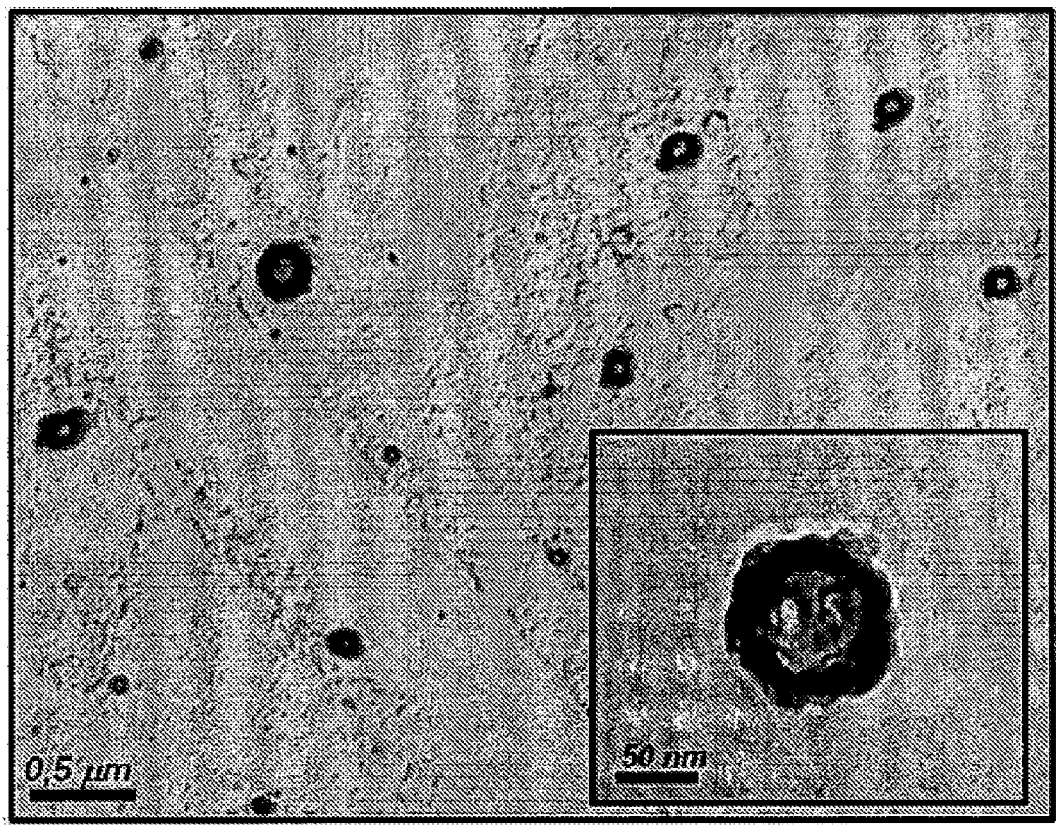

FIG. 4 shows the size distribution of the vesicles (hydrodynamic radius) obtained by light scattering. FIG. 5 shows an image from transmission electron microscopy obtained for these same vesicles.

EXAMPLE 6

Encapsulation of an Active Ingredient in a Micellar Vesicle

Doxorubicin and docetaxel were encapsulated in micellar vesicles based on the hyaluronic acid-block-poly(γ-benzyl L-glutamate) copolymer from Example 1 by nanoprecipitation.

The active ingredient was dissolved in DMSO or Tris buffer at weight ratios of active ingredient to copolymer of 0.1:1, 0.2:1 and 0.3:1. The copolymer block is dissolved in the organic phase of DMSO at 55° C. This solution is added to the aqueous solution (Tris buffer pH=7.4), stirring continuously at 55° C., or vice versa. The free active ingredient and the DMSO were removed by dialysis (molecular weight cut-off threshold of 2 kDa) against Tris buffer.

The quantity of doxorubicin encapsulated (in the hydrophobic or hydrophilic part of the vesicles) and the efficiency of encapsulation were determined by disrupting the filled vesicles in a DMSO:Tris mixture (80:20). After centrifugation for 1 h, the sample was filtered and measured by UV spectroscopy at 485 nm. Quantification was performed from the calibration curve of doxorubicin in the DMSO:Tris mixture (80:20). The amount of docetaxel encapsulated and the efficiency of encapsulation were determined from reconstitution of a dry extract of vesicle containing docetaxel in ethanol. Next, the filtered sample was measured by UV spectroscopy at 230 nm. Quantification was performed from the calibration curve of doxorubicin in ethanol.

Amount encapsulated=(mass of active ingredient in the filled vesicle/mass of vesicle)×100

Efficiency of encapsulation=(mass of active ingredient in the filled vesicle/initial mass of active ingredient)×100

The results are presented in Table 1 below.

TABLE 1

| | Weight ratio active ingredient:copolymer | | |
|---|---|---|---|
| | 0.1:1 | 0.2:1 | 0.3:1 |
| doxorubicin (DMSO phase) | | | |
| Amount encapsulated (%) | 4.95 ± 0.49 | 9.74 ± 0.95 | 11.82 ± 1.12 |
| Efficiency of encapsulation (%) | 49.47 ± 4.94 | 48.70 ± 4.74 | 39.41 ± 3.72 |
| doxorubicin (aqueous phase) | | | |
| Amount encapsulated (%) | 5.32 ± 0.58 | 10.51 ± 0.32 | 12.43 ± 1.19 |
| Efficiency of encapsulation (%) | 53.50 ± 6.21 | 52.56 ± 1.60 | 41.45 ± 3.97 |
| docetaxel (DMSO phase) | | | |
| Amount encapsulated (%) | 2.77 ± 0.27 | 9.81 ± 0.66 | 13.60 ± 0.73 |
| Efficiency of encapsulation (%) | 27.68 ± 2.69 | 49.07 ± 3.32 | 46.78 ± 2.32 |

The results show high levels of encapsulation of the order of 10% and an efficiency of encapsulation of around 50%.

EXAMPLE 7

Release of an Active Ingredient Encapsulated in a Micellar Vesicle

The desired quantity (for example, a volume of 4 mL at a concentration of 1 mg/mL) of vesicles filled with doxorubicin and docetaxel is poured into a dialysis tube (Spectra/Por® Float-A-Lyzer®, Dialysis Tubes, molecular weight cut-off threshold of 25 kDa, diameter 10 mm, volume 10 mL). The dialysis tube is placed vertically in a 50-mL measuring cylinder. The system is maintained at 37° C.±2 and covered with Parafilm to prevent evaporation. In order to maintain the required osmotic conditions, 2 mL was taken from the exterior of the dialysis tube for each sampling time and replaced with the same volume of Tris buffer.

In the case of doxorubicin, sampling is performed in the dialysis tube, then reinserted as it is after analysis.

For docetaxel, sampling is performed from the exterior of the dialysis tube. The dialysis medium contained 50 mL of Tris buffer (pH 7.4) with 2% v/v of ethanol to increase the solubility of the docetaxel released and avoid aggregation of the free docetaxel.

Quantification is carried out based on the calibration curve of the free active ingredients in their respective solvents.

Figure 6:
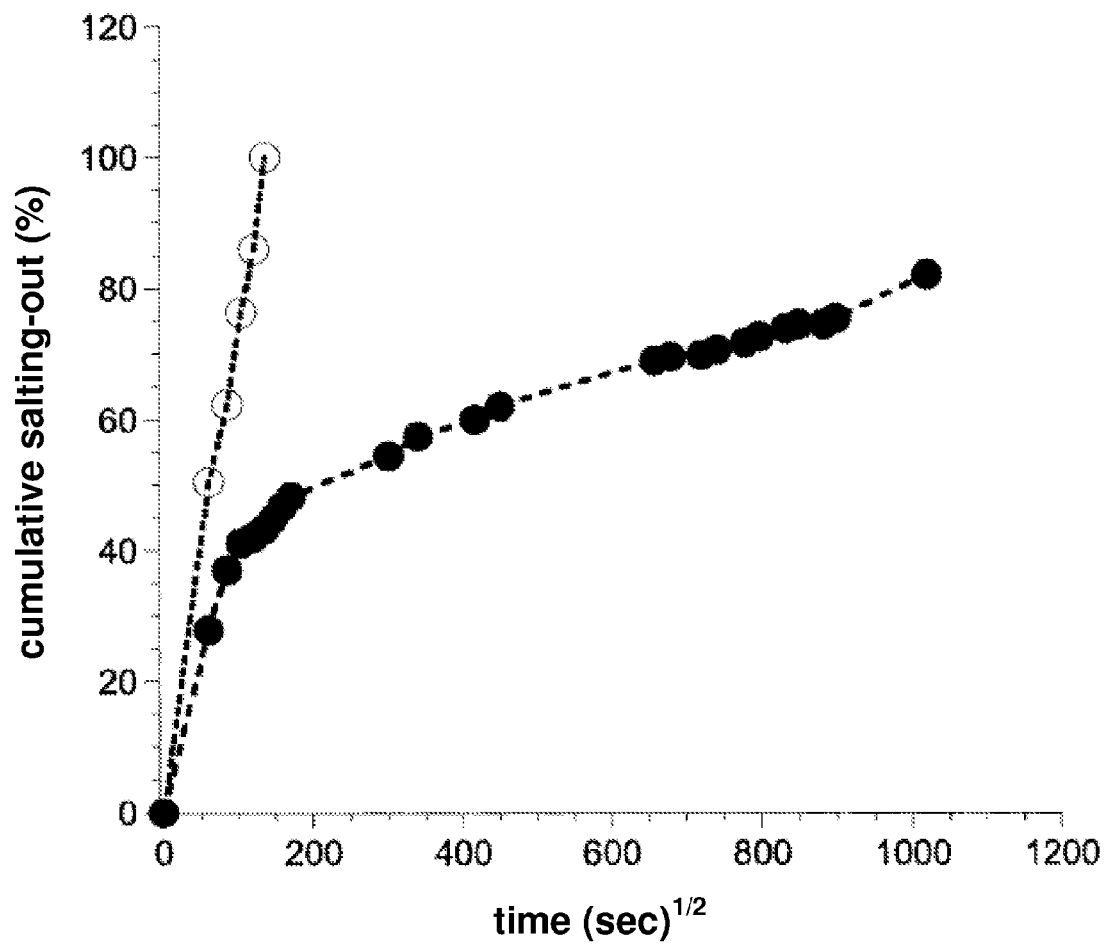
Figure 7:
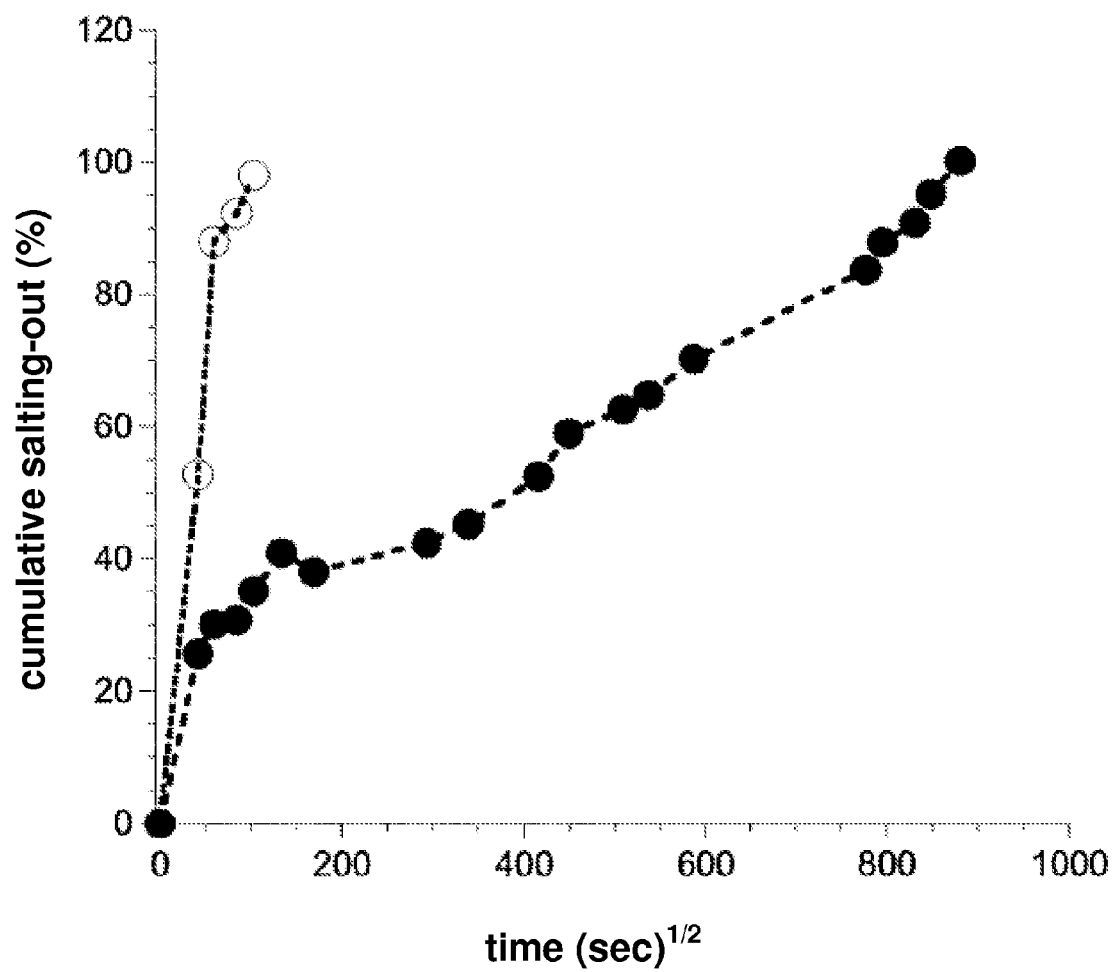

The release profiles expressed as percentage cumulative salting out as a function of time (in second $^{1/2}$) are shown in FIGS. 6 (doxorubicin) and 7 (docetaxel).

The free active ingredient is represented by the symbol -○-(open circle) and the release of the encapsulated active ingredient is represented by the symbol -●-(filled circle).

The results clearly show that the release of these two active ingredients can be controlled over several days with much slower kinetics than that of the free active ingredient. Release appears to follow a model of uniform diffusion.

EXAMPLE 8

Release and Toxicity In Vitro of an Active Ingredient Encapsulated in a Micellar Vesicle Experiments of toxicity and release in vitro were performed using vesicles based on hyaluronic acid-block-poly (γ-benzyl L-glutamate) diblock copolymer prepared in Example 6, containing 11% of doxorubicin.

The in-vitro experiments were performed on cells of rat glioma C6, in Dulbecco's modified Eagle's medium (DMEM) containing 5% of foetal calf serum. The C6 cells ($5 \times 10^5$ cells) are placed in bottles of 10 cm diameter and are grown in 10 ml of culture medium containing penicillin (10000 µg/mL), streptomycin (10000 µg/mL) and amphotericin B (25 µg/mL) [Invitrogen Corporation] in an incubator at 37° C. in a controlled atmosphere with 5% $CO_2$.

For the tests of cellular viability (or toxicity), C6 cells were incubated in a 24-well plate ($15 \times 10^4$ cells per well), for 24 h. Viability was determined by a conventional test with tetrazolium salt MTT (3-(4,5-dimethylthiazol-2-yl)-2,5-diphenyl tetrazolium bromide). The tetrazolium that it contains is reduced to formazan by the mitochondrial succinate dehydrogenase of the active living cells. The colour of the medium then changes from yellow to purplish-blue. The intensity of this coloration is proportional to the number of living cells present during the test. Analysis is performed by spectrophotometry (U-2800A, HITACHI), measuring the absorbance at 570 nm. The measurements are standardized by a control experiment, for which the MTT test is performed without cells. In this way the IC50 value is determined for a time of 48 h, corresponding to the concentration for which half of the cells remain viable.

For free doxorubicin, a value of 0.84 µM is obtained.

For vesicles encapsulating doxorubicin, a value 10 times greater (IC50=8.4 µM) is obtained. The vesicle alone (without doxorubicin) did not show any toxicity under the experimental conditions (concentration up to 200 µM, time up to 72 h).

EXAMPLE 9

Study of Cellular Internalization of Micellar Vesicles Containing an Active Ingredient Cellular internalization was monitored in vitro by fluorescence microscopy. For this, the C6 cells were incubated (15×10$^4$ cells) in a plate with 4 wells of 16 mm. The vesicles containing doxorubicin at a concentration of 4.54 µM were incubated for times of 3 h, 6 h and 24 h at 37° C. in a controlled atmosphere with 5% $CO_2$. For each observation time, the cells are washed twice with PBS buffer, fixed on a microscope cover-slip with 4% of paraformaldehyde (PF4) in PBS buffer, left in the dark at ambient temperature for 30 min, then washed once with PBS buffer and once with pure water. Microscopy is performed with a Zeiss fluorescence microscope (magnification ×63; $\lambda_{excitation}$=546 nm and $\lambda_{emission}$=590 nm).

Figure 8:
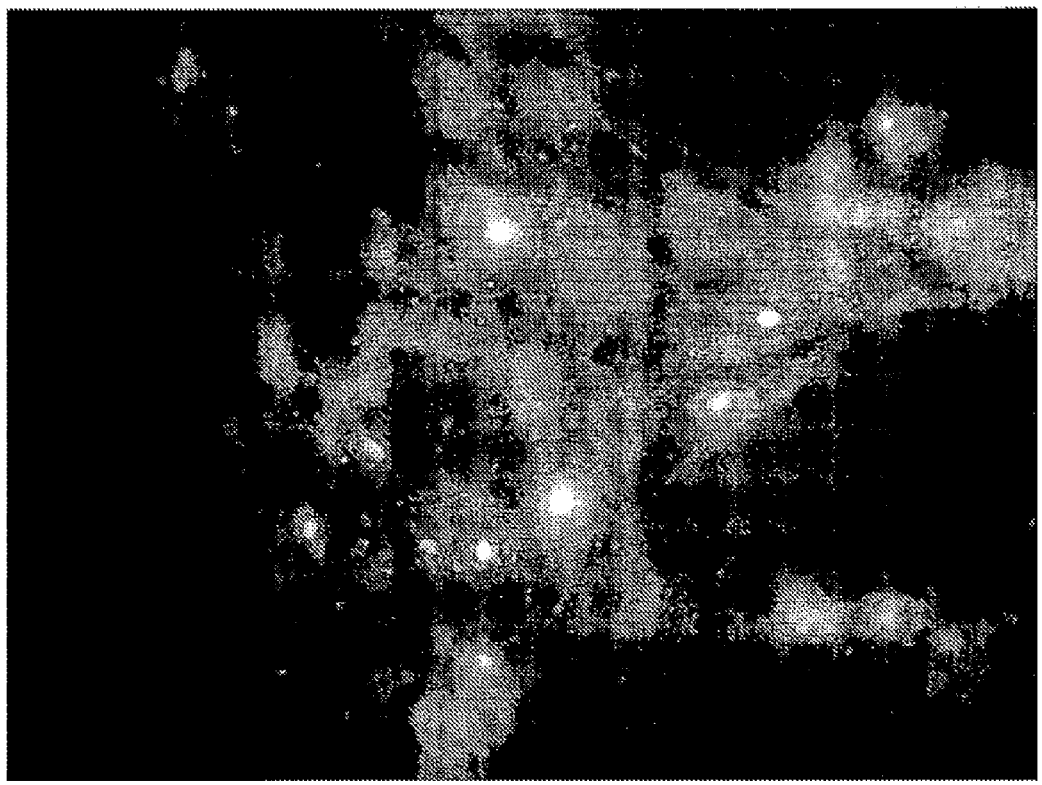

Monitoring by fluorescence microscopy in vitro on C6 cells after incubation for 24 h in the presence of the vesicles containing doxorubicin is shown in FIG. 8. The vesicles containing doxorubicin are internalized by endocytosis. After incubation for 24 h, strong accumulation is observed in the endosomes, resulting from internalization of the vesicles containing doxorubicin. The cells show large excrescences, which are characteristic of this internalization.

EXAMPLE 10

Test of Skin Irritation in the Rabbit

A dispersion at 1% (w/v) of hyaluronic acid-block-poly(γ-benzyl L-glutamate) diblock copolymer from Example 1 was used.

This dispersion was applied at a dose of 0.5 mL, under semi-occlusive dressing, for 4 h on an area of healthy skin in 3 rabbits.

The experimental protocol is that of OECD Directive No. 404 dated 24 Apr. 2002 and of test method B.4 of Directive EC 440/2008.

No skin reaction (erythema or oedema) was observed on the treated area, regardless of when it was examined (24 h, 48 h and 72 h after removing the dressing).

EXAMPLE 11

Study of Potential for Skin Irritation in the Mouse

A dispersion at 1% (w/v) of hyaluronic acid-block-poly(γ-benzyl L-glutamate) diblock copolymer from Example 1 was used.

The dispersion of copolymer was applied on the dorsal surface of the ear of a line of female mice.

3 groups of 4 animals each were treated for three consecutive days (D1, D2, D3) with 50 µl (25 µl per ear) of undiluted test dispersion (100%), on the one hand, and of test dispersion diluted in dimethylformamide (DMF) at concentrations of 25% and 50% (v/v). A supplementary group of 4 animals was treated with DMF.

On day 6, the proliferation of lymphocytes in the lymph nodes draining the ear was determined by cell counting.

The experimental protocol was established according to OECD Directive No. 429 dated 24 Apr. 2002 and test method B. 42 of Directive EC 440/2008.

The results showed that:
a) no mortality or sign of systemic toxicity was observed in the animals tested and the control animals;
b) no skin reaction was observed at concentrations of 25%, 50% and 100%.

The results show that the dispersion of copolymer according to the invention is non-irritant at the three concentrations tested.

EXAMPLE 12

Evaluation of the Maximum Dose Tolerated by the Intravenous Route in the Mouse A dispersion at 1% (w/v) of hyaluronic acid-block-poly(γ-benzyl L-glutamate) diblock copolymer from Example 1 was used.

The dispersion of copolymer was administered intravenously in a male and a female Swiss mouse at an administration volume of 10 mL/kg. Taking the density of the formulation into account, this administration corresponds to a dose of 10 g/kg.

No mortality was observed for the 14 days of the study. Macroscopic examination of the animals at the end of the treatment did not show any change associated with the treatment.

The results show that the maximum tolerated dose (MTD) of the dispersion of copolymer according to the invention by the intravenous route is greater than 10 g/kg in the mouse.

EXAMPLE 13

Study of Targeting of CD 44 Receptors Linked to Hyaluronic Acid by Competitive Inhibition in the Presence of Free Hyaluronic Acid The human cell line MCF-7, which expresses CD 44 receptors significantly, was used.

In order to confirm the cellular internalization of encapsulated doxorubicin by endocytosis via specific receptors of hyaluronic acid, a competitive inhibition test was performed by first adding free hyaluronic acid to the incubation medium so as to block to a certain extent the receptors of hyaluronic acid on the surface of the cells.

The cells (0.1×10$^6$) were incubated for 1 h at 37° C. with pure doxorubicin or doxorubicin encapsulated in the micellar vesicles from Example 6 (doxorubicin concentration=10 µM) in dishes of 40 mm diameter in a serum-free medium, in the presence or in the absence of free hyaluronic acid (MW=5000 g/mol), at a concentration of 2 mg/mL. The cells were then washed twice with PBS buffer and collected by centrifugation (1000 rpm for 10 min). The cells were then resuspended in 300 µL of PBS buffer prior to measurement.

The samples were collected on a FACS Calibur flow cytometer (Beckton Dickinson) and analysed using the Cell Quest software supplied by the manufacturer. For each analysis, at least 10000 cells were counted.

It is found that the presence of free hyaluronic acid significantly reduces the mean fluorescence intensity (MFI) of free doxorubicin.

Figure 9:
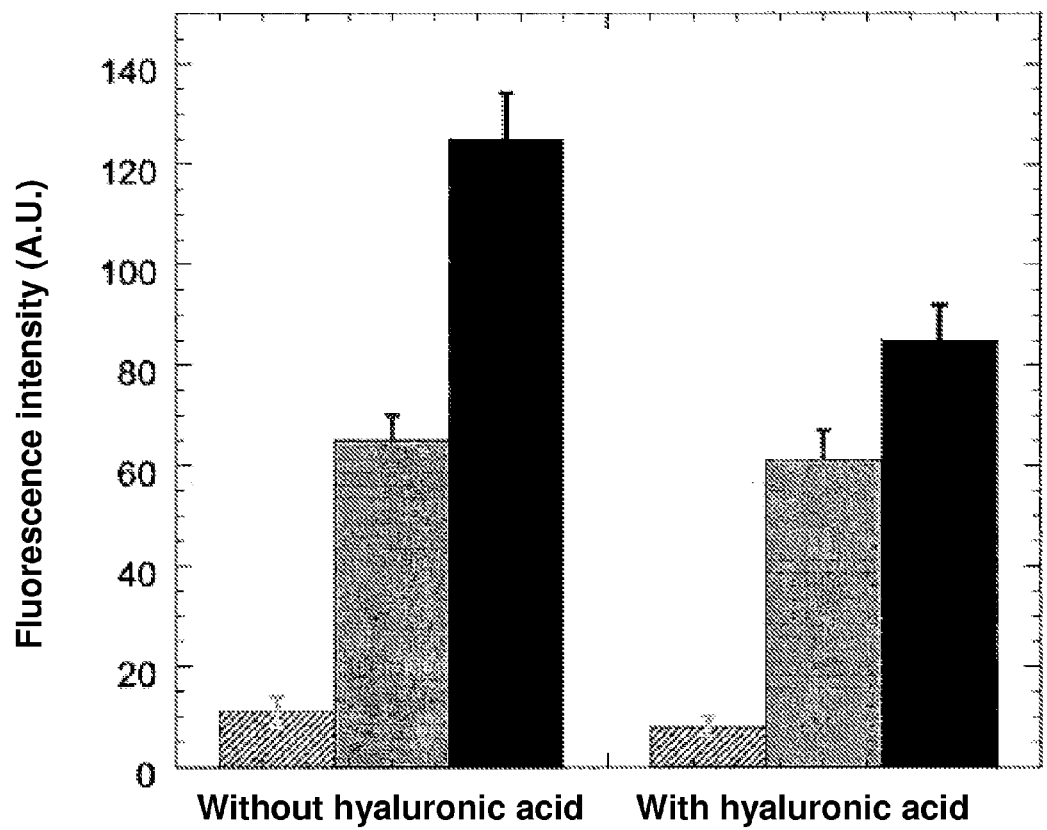

FIG. 9 shows the relative fluorescence intensity measured in arbitrary units (AU) in the MCF-7 cells measured after incubation in the presence of encapsulated doxorubicin (black column), of free doxorubicin (grey column) and without doxorubicin (cross-hatched column), in the presence or in the absence of free hyaluronic acid.

The results show that, for free doxorubicin, incubation in the presence of free hyaluronic acid has little or no effect on internalization (no significant decrease in mean fluorescence intensity).

This can be explained by the fact that free doxorubicin diffuses freely in the cells, as internalization is not linked to mediation of the CD 44 receptors.

In contrast, the intensity of fluorescence in the presence of free hyaluronic acid decreases significantly for the encapsulated doxorubicin.

These results show the role of the hyaluronic acid receptors in endocytosis of the micellar vesicles based on hyaluronic acid according to the invention, permitting intracellular delivery of doxorubicin.

EXAMPLE 14

Evaluation In Vivo of the Antitumour Efficacy of Encapsulated Doxorubicin

1/Experimental Protocol

Female Sprague-Dawley rats aged 8 weeks (120-140 g) were used in a study of tumour regression.

7,12-dimethylbenz[α]anthracene (DMBA) was administered orally (in soya oil) to the animals in 3 doses of 45 mg/kg at one-week intervals, to generate the tumour.

The treatment with doxorubicin was given 10 weeks after the last dose of DMBA. The width of the tumour (w) and its length (l) were recorded with callipers and the size of the tumour was calculated from the formula (w×l²/2).

After 10 weeks from tumour induction, the animals with tumours were separated and divided randomly into different treatment groups, then treated with a single dose of 250 μl of doxorubicin by intravenous route at 5 mg/kg, either in the form of free doxorubicin, or in the form of doxorubicin encapsulated in the micellar vesicles of Example 6.

The control group received a single dose of 250 μl of PBS buffer (pH 7.4) by the intravenous route.

The study was terminated 30 days after treatment.

Observation of the survival of the animals with a tumour, which were treated, was continued until 60 days after treatment.

2/Antitumour Activity of Encapsulated Doxorubicin

Figure 10:
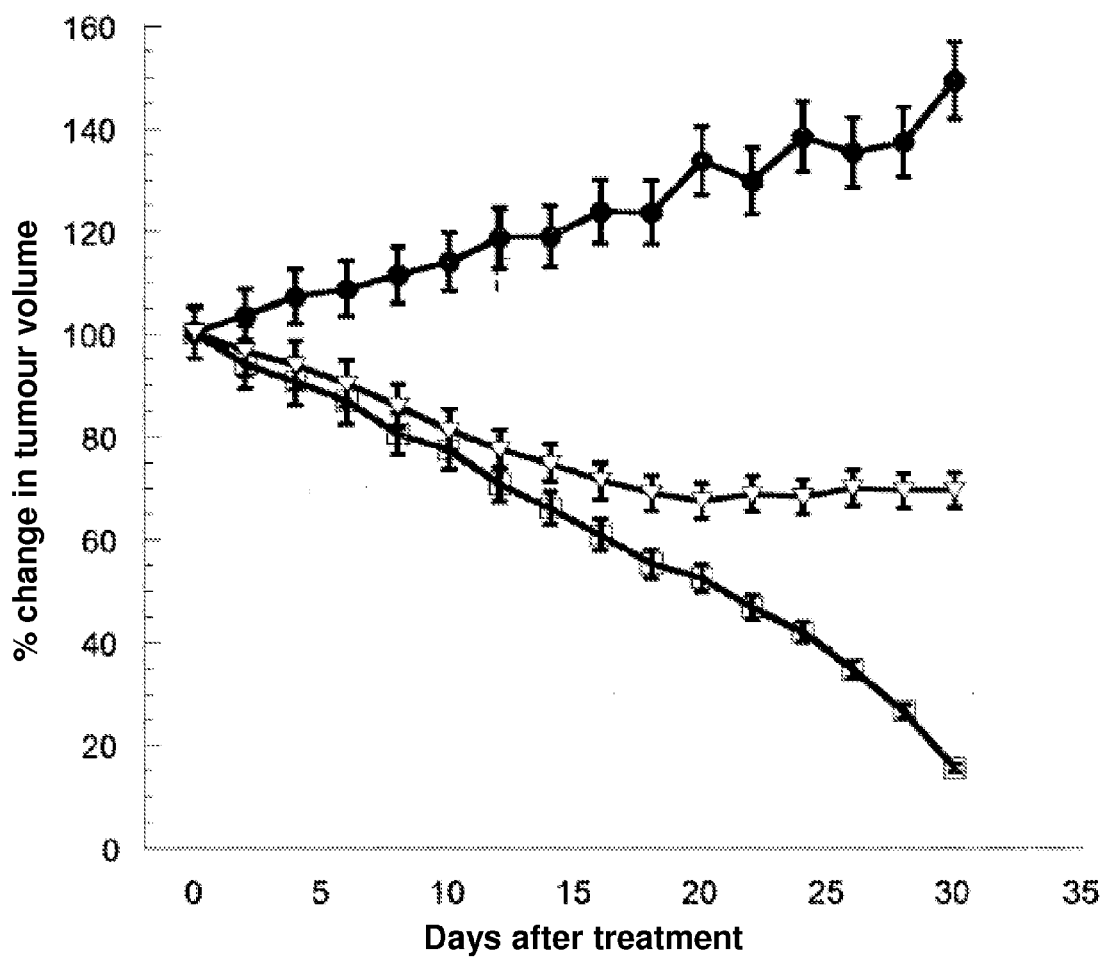

FIG. 10 shows the variation of tumour volume as a function of time, following treatment with free doxorubicin (curve represented by the symbol -∇-), encapsulated doxorubicin (curve represented by the symbol - -) or PBS (curve represented by the symbol -●-).

The results show that free doxorubicin and the encapsulated doxorubicin significantly inhibit tumour growth in comparison with the control group treated with PBS. However, the encapsulated doxorubicin causes far greater tumour suppression than free doxorubicin.

In fact, after 15 days of treatment, it is observed that the tumour continues to regress with encapsulated doxorubicin, whereas regression reaches a plateau with free doxorubicin.

Figure 11:
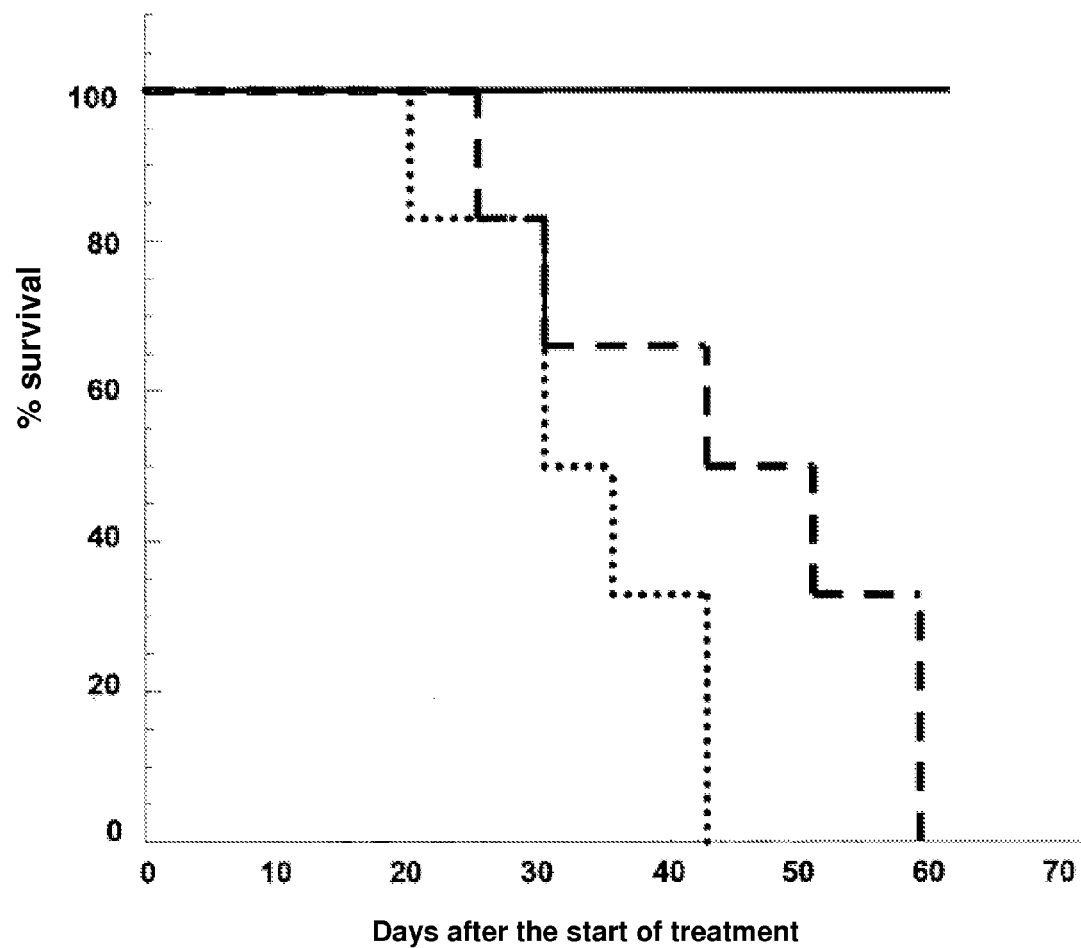

The Kaplan-Meier survival curve presented in FIG. 11, where each point represents the mean±standard error of the mean (n=6), shows the survival time of the animals after the start of treatment, for animals that received, by intravenous administration, encapsulated doxorubicin (solid straight line), free doxorubicin (dashed straight line) and the control group (dotted straight line).

The results show absence of mortality at 60 days for the animals treated with the encapsulated doxorubicin.

3/Cardiotoxicity

One of the main, well-known side-effects of doxorubicin is its cardiotoxicity. The latter can be evaluated by measuring the production of specific enzymes, principally lactate dehydrogenase and creatine kinase.

Measurement of serum level of lactate dehydrogenase and of creatine kinase in the various groups of animals in the above experiments shows that induction of lactate dehydrogenase and of creatine kinase is less in the animals treated with encapsulated doxorubicin in comparison with those treated with free doxorubicin, as shown in FIGS. 12A (creatine kinase) and 12B (lactate dehydrogenase).

The results show that encapsulated doxorubicin induces a low level of lactate dehydrogenase and of creatine kinase, meaning a decrease in cardiotoxicity of doxorubicin encapsulated in the micellar vesicles according to the invention.

This decrease in cardiotoxicity is in agreement with the significant reduction of side-effects and mortality that was observed when using encapsulated doxorubicin.

The invention claimed is:

1. A micellar vesicle, comprising an amphiphilic polysaccharide-block-polypeptide diblock linear copolymer composed of a polysaccharide block of natural or synthetic saccharide units with a polypeptide block of natural or synthetic peptide units, wherein:
   said polysaccharide block and said polypeptide block are joined by their ends;
   said polysaccharide is hyaluronic acid;
   said polypeptide block is hydrophobic; and
   said vesicle encapsulates at least one molecule of interest,
   said micellar vesicle being capable of targeting cellular receptors and to allow targeted release of the encapsulated molecule of interest by receptor mediated endocytosis.

2. The micellar vesicle according to claim 1, wherein said diblock copolymer comprises from 5 to 100 saccharide units, and from 5 to 100 peptide units.

3. The micellar vesicle according to claim 1, wherein the polypeptide, in which the amino acid of which it is constituted can be in the optically active form L or D or in the racemic form DL, is selected from the group consisting of poly(alanine), poly(isoleucine, poly(leucine), poly(methionine), poly (phenylalanine), poly(proline), poly(tryptophan), poly(valine), poly(benzyl glutamate), poly(alkyl glutamate), poly (trifluoroacetyl-Lysine), poly(sarcosine), poly (hydroxyethyl-asparagine), poly(hydroxyalkyl-asparagine), poly(hydroxyalkyl-aspartamide), poly(benzyl aspartate) and derivatives thereof.

4. The micellar vesicle according to claim 1, wherein said polysaccharide is hydrophilic and said polypeptide is hydrophobic under physiological conditions.

5. The micellar vesicle according to claim 4, wherein the polypeptide is selected from the group consisting of poly(γ-benzyl L-glutamate) and poly(ε-trifluoroacetyl-L-lysine).

6. The micellar vesicle according to claim 1, wherein said at least one molecule of interest is selected from those molecules used for preventing or treating a pathology or for restoring a biological function, in vitro or in vivo, in an animal or on isolated cells.

7. The micellar vesicle according to claim 6, wherein said molecule of interest is selected from the group consisting of an active ingredient of a medicament, a peptide, a protein, a hormone, an enzyme, a nucleic acid, an oligonucleotide, an antigen, an antibody, an interferon, a growth factor, a modulator of enzyme activity, a cell receptor activator or inhibitor, and a vitamin.

8. A pharmaceutical composition comprising a micellar vesicle according to claim 1 and a pharmaceutically acceptable excipient.

9. The micellar vesicle according to claim 1, wherein the vesicle further comprises two compartments of different polarity.

10. The micellar vesicle according to claim 9, wherein the vesicle has a hydrophobic membrane and a hydrophilic internal cavity.

11. The micellar vesicle according to claim 2, wherein said diblock copolymer comprises from 10 to 50 saccharide units.

12. The micellar vesicle according to claim 2, wherein said diblock copolymer comprises from 10 to 50 peptide units.

13. The micellar vesicle according to claim 2, wherein said diblock copolymer comprises from 10 to 50 saccharide units and from 10 to 50 peptide units.

14. The micellar vesicle according to claim 6, wherein said animal is a human.

* * * * *